United States Patent
Berger et al.

(10) Patent No.: US 6,583,279 B1
(45) Date of Patent: Jun. 24, 2003

(54) SEQUENCES AND METHODS FOR DETECTION OF HEPATITIS B VIRUS

(75) Inventors: Dolores M. Berger, Baltimore, MD (US); William A. Nussbaumer, Timonium, MD (US); Thomas L. Fort, Finksburg, MD (US); Tobin J. Hellyer, Owings Mills, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/770,532

(22) Filed: Jan. 26, 2001

(51) Int. Cl.[7] .................. C07H 21/00; C07H 21/04; G01N 33/576; C12Q 1/68; C12P 19/34
(52) U.S. Cl. ................ 536/24.3; 536/24.33; 536/24.32; 536/23.1; 536/23.72; 536/23.32; 536/23.33; 435/5; 435/7.95; 435/8; 435/91.33
(58) Field of Search ................ 435/5, 91.33, 7.95, 435/8; 536/23.1, 23.72, 24.3, 23.32, 23.33, 24.32, 24.33

(56) References Cited

U.S. PATENT DOCUMENTS

| | | | |
|---|---|---|---|
| 4,562,159 A | 12/1985 | Shafritz | |
| 4,710,463 A | 12/1987 | Murray | |
| 5,593,825 A | 1/1997 | Carman et al. | |
| 5,614,362 A | 3/1997 | Urdea et al. | |
| 5,709,997 A | 1/1998 | Marshall et al. | |
| 5,728,518 A | 3/1998 | Carmichael | |
| 5,736,316 A | 4/1998 | Irvine et al. | |
| 5,736,334 A | 4/1998 | Spies | |
| 5,780,219 A | 7/1998 | McDonough et al. | |
| 5,856,459 A | 1/1999 | Frank et al. | |

FOREIGN PATENT DOCUMENTS

| | | |
|---|---|---|
| EP | 0 198 474 B1 | 4/1986 |
| EP | 0 719 863 A1 | 4/1986 |

OTHER PUBLICATIONS

Ausubel et al. (Short Protocols in Molecular Biology, 1999, Fourth Edition, Edited by Ausubel et al. Published by John Wiley & Sons, Inc., p. 6–8).*
Bains Molecular Biology and Biotechnology 1995, Edited by Meyers et al. pp. 441–443.*
U. Norborg et al., Automated Quantitative Analysis of Hepatitis B Virus DNA by using the Cobas Amplicor HBV Monitor Test, J. of Clinical Microbiology, Sep. 1999, p. 2793–2797; A. Abe et al., Quantitation of Hepatitis B Virus Genomic DNA by Real–Time Detection PCR, J. of Clinical Microbiology, Sep. 1999, p. 2899–2903; K. Kidd–Ljunggren, Variability in Hepatitis B Virus DNA: Phylogenetic, Epidemiological and Clincal Implications, Scand.
J Infect Dis 28:111–116, 1996; L.O. Magnius, Subtypes, Genotypes and Molecular Epidemiology of the Hepatitis B Virus as Reflected by Sequence Variabiliity of the S–Gene, Interrvirology 1995;38:24–34; T.J. Harrison, Genetic Variation in Hepatitis B Virus, European Journal of Gastroenterology & Hepatology, 1996, vol. 8, No. 4.

* cited by examiner

Primary Examiner—James Housel
Assistant Examiner—Bao Qun Li
(74) Attorney, Agent, or Firm—Allan M. Kiang

(57) ABSTRACT

Primers and probes derived from the HBV DNA polymerase gene which facilitate detection and/or quantification of all presently known genotypes of HBV. Disclosed sequences may be used in a variety of primer and probe constructs for detection of HBV nucleic acids.

3 Claims, No Drawings

US 6,583,279 B1

SEQUENCES AND METHODS FOR DETECTION OF HEPATITIS B VIRUS

FIELD OF THE INVENTION

The present invention relates to materials and methods for detection of Hepatitis B viral nucleic acids, in particular to probes and primers for detection of Hepatitis B in hybridization and amplification assays.

BACKGROUND OF THE INVENTION

Hepatitis B virus (HBV) is a partially double-stranded DNA virus which uses a unique replication mechanism incorporating an intermediate reverse transcription step. It is a major causative agent of chronic hepatitis and has been implicated in liver cirrhosis and hepatocellular carcinoma. Accurate identification and quantitation of HBV DNA is important not only for detecting HBV infection but also for monitoring the efficacy of antiviral treatments. A simple assay for HBV DNA using branched-DNA (bDNA) probes has been used for quantitation but was found to be insufficiently sensitive to monitor serum virus levels in patients undergoing antiviral treatment. More recently, HBV DNA has been detected and quantitated in more sensitive PCR assays, using both the Amplicor™ HBV Monitor test and the TaqMan™ technology for real-time detection.

The present invention provides probes and primers for detection of HBV nucleic acids which may provide a more rapid and sensitive means for detecting HBV than immunological and culture-based methods. Further the probes and primers of the invention may allow more reliable detection of naturally occurring variants of HBV, as they are based on an analysis of conserved regions of the HBV DNA polymerase gene.

SUMMARY OF THE INVENTION

The present invention provides primers and probes derived from the HBV DNA polymerase gene which are predicted to facilitate detection and/or quantification of all presently known genotypes of HBV (A–F). That is, a single amplification primer pair according to the invention should efficiently amplify all known genotypes of HBV, which may then be detected in a single detection step using the detector probes and primers of the invention.

DETAILED DESCRIPTION OF THE INVENTION

The primers, hybridization probes and detector primers of the present invention are complementary to regions of the HBV DNA polymerase gene. Design of the disclosed primers and probes was based on relatively conserved regions in an alignment of multiple HBV DNA polymerase gene sequences. One goal was to develop probes and primers which, in spite of heterogeneity in the gene sequence, would be expected to for provide amplification, detection and/or quantitation of all presently known HBV genotypes with approximately equal efficiency. In some cases this was accomplished by overlapping the hybridization site of the 5' ends of certain of the detector probes with the hybridization site of the 3' end an amplification primer. This approach took advantage of short stretches of relative sequence conservation in the primer hybridization region and avoided much of the sequence heterogeneity evident in the intervening region between the two amplification primers. This technique also allowed use of a smaller target sequence, which would be expected to improve amplification efficiency.

As used herein, an amplification primer is an oligonucleotide for amplification of a target sequence by extension of the oligonucleotide after hybridization to the target sequence or by ligation of multiple oligonucleotides which are adjacent when hybridized to the target sequence. At least a portion of the amplification primer hybridizes to the target. This portion is referred to as the target binding sequence and it determines the target-specificity of the primer. In addition to the target binding sequence, certain amplification methods require specialized non-target binding sequences in the amplification primer. These specialized sequences are necessary for the amplification reaction to proceed and typically serve to append the specialized sequence to the target. For example the amplification primers used in Strand Displacement Amplification (SDA) include a restriction endonuclease recognition site 5' to the target binding sequence (U.S. Pat. No. 5,455,166 and U.S. Pat. No. 5,270,184). Nucleic Acid Sequence Based Amplification (NASBA) Self Sustaining Sequence Replication (3SR) and transcription based amplification primers require an RNA polymerase promoter linked to the target binding sequence of the primer. Linking such specialized sequences to a target binding sequence for use in a selected amplification reaction is routine in the art. In contrast, amplification methods such as PCR which do not require specialized sequences at the ends of the target, generally employ amplification primers consisting of only target binding sequence.

As used herein, the terms "primer" and "probe" refer to the function of the oligonucleotide. A primer is typically extended by polymerase or ligation following hybridization to the target but a probe typically is not. A hybridized oligonucleotide may function as a probe if it is used to capture or detect a target sequence, and the same oligonucleotide may function as a primer when it is employed as a target binding sequence in an amplification primer. It will therefore be appreciated that any of the target binding sequences disclosed herein for amplification, detection or quantitation of HBV may be used either as hybridization probes or as target binding sequences in primers for detection or amplification, optionally linked to a specialized sequence required by the selected amplification reaction or to facilitate detection.

Based on the alignment of multiple HBV DNA polymerase gene sequences, the following amplification primers were designed for testing in SDA reactions. Target binding sequences are underlined. The remaining 5' portion of the sequence comprises the restriction endonuclease recognition site (RERS) that is required for the SDA reaction to proceed plus a generic non-target-specific tail sequence. It will be readily apparent that the target binding sequences may be used alone to amplify the target in reactions which do not require specialized sequences or structures (e.g., PCR) and that other specialized sequences required by amplification reactions other than SDA (e.g., an RNA polymerase promoter) may be substituted for the RERS-containing sequence shown below. "R" and "L" in the primer name indicates "right" and "left" primers, respectively, when the oligonucleotides are used in amplification reactions:

| AMPLIFICATION PRIMERS | | |
|---|---|---|
| HBV1AL1 | CGATTCCGCTCCAGACTTCTCGGGCCCCTGCTCGTGTTA | SEQ ID NO:1 |
| HBV1AL2 | CGATTCCGCTCCAGACTTCTCGGGCCCCTGCTCGTGTT | SEQ ID NO:2 |
| HBV1AL3 | CGATTCCGCTCCAGACTTCTCGGGACCCCTGCTCGTGTT | SEQ ID NO:3 |
| HBV1AR1 | ACCGCATCGAATGCATGTCTCGGGGGTATTGTGAGGATT | SEQ ID NO:4 |
| HBV1AR2 | ACCGCATCGAATGCATGTCTCGGGTGAGGATTATTGTCAAC | SEQ ID NO:5 |
| HBV1AR3 | ACCGCATCGAATGCATGTCTCGGGTATTGTGAGGATT | SEQ ID NO:6 |

The following detector primers were also designed for detection of amplification products produced using the amplification primers. They hybridize to the target sequence downstream of or overlapping an amplification primers so that they are displaced during the amplification reaction. The detector primer hybridization site may or may not overlap the hybridization site of the amplification primer. An advantage of this detection method is that the target sequence can be detected and/or quantified as the amplification reaction is occurring, i.e., in "real-time" rather than at an endpoint. The target binding sequences of the primers are underlined. The remaining portion of the sequence forms a hairpin structure which is typically labeled to facilitate detection of amplification products, for example as described in U.S. Pat. No. 5,928,869. It will be readily apparent that the target sequence may be used alone for detection (typically linked to a detectable label) and that other detectable sequences and labels may be substituted for the hairpin as is known in the art (e.g., G-quartets, linear sequences for specific probe hybridization, or restriction sites). See, for example, U.S. Pat. No. 5,547,861; U.S. Pat. No. 5,928,869; U.S. Pat. No. 5,593,867; U.S. Pat. No. 5,550,025; U.S. Pat. No. 5,935,791; U.S. Pat. No. 5,888,739; U.S. Pat. No. 5,846,726.

| DETECTOR PRIMERS | | |
|---|---|---|
| HBV1DL1 | TAGCACCCGAGTGCTAGGCGGGGTTTTTCTTGTTGACA | SEQ ID NO:7 |
| HBV1DL2 | TAGCACCCGAGTGCTAGGCGGGGTTTTTCTTGTTGACAA | SEQ ID NO:8 |
| HBV1DR1 | TAGCACCCGAGTGCTTTGTCAACAAGAAAAACCCCGCCT | SEQ ID NO:9 |
| HBV1DL3 | TAGCACCCGAGTGCTGCTCGTGTTACAGGCGG | SEQ ID NO:10 |
| HBV1DL4 | TAGCACCCGAGTGCTCTCGTGTTACAGGCGG | SEQ ID NO:11 |
| HBV1DR2 | TAGCACCCGAGTGCTTTGTGAGGATTCTTGTCAAC | SEQ ID NO:12 |
| HBV1DR3 | TAGCACCCGAGTGCTTTGTGAGGATTATTGTCAAC | SEQ ID NO:13 |
| HBV1DR4 | TAGCACCCGAGTGCTGTGAGGATTCTTGTCAAC | SEQ ID NO:14 |
| HBV1DR5 | TAGCACCCGAGTGCTGTGAGGATTATTGTCAAC | SEQ ID NO:15 |

SEQ ID NOs:7–9 are conventional non-overlapping detector primers which contain a hairpin as described in U.S. Pat. No. 5,928,869. SEQ ID NOs:10–15 also contain the hairpin but the 5' end of the target binding sequences overlap with the 3' end of the target binding sequences of the upstream amplification primers.

Bumper primers used in SDA (BR and BL) and detector probes (PD) for use in post-amplification primer extension detection assays were also designed. The entire sequence of each of these oligonucleotides consists of target binding sequence:

| BUMPER PRIMERS/DETECTOR PROBES | | |
|---|---|---|
| HBV1BL1 | CATCAGGATTCCTAG | SEQ ID NO:16 |
| HBV1BR1 | ACGAGTCTAGACTC | SEQ ID NO:17 |
| HBV1BR2 | AAAATTGAGAGAAGTC | SEQ ID NO:18 |

-continued

| BUMPER PRIMERS/DETECTOR PROBES | | |
|---|---|---|
| HBV1PDL | GGTTTTTCTTGTTGACA | SEQ ID NO:19 |
| HBV1PDR | AAGAAAAACCCCGCCT | SEQ ID NO:20 |

The primers and probes set forth above were selected to minimize the effects of heterogeneity in the targeted region of the DNA polymerase gene. Mismatches were confined to the middle or the 5' end of the primers and probes to permit efficient 3' extension upon hybridization to the target sequence.

Because the target binding sequence confers target specificity on the primer or probe, it should be understood that the target binding sequences exemplified above for use as particular components of a specific amplification reaction may also be used in a variety of other ways for detection of the known genotypes of HBV. For example, the target binding sequences of SEQ ID NOs:1–20 may alternatively be used as hybridization probes for direct detection of HBV, either without prior amplification or as a post-amplification assay.

Such hybridization methods are well known in the art and typically employ a detectable label associated with or linked to the target binding sequence to facilitate detection of hybridization. Further, essentially all of the target binding sequences set forth above may be used as amplification primers in amplification reactions which do not require additional specialized sequences (such as PCR) or appended to the appropriate specialized sequences for use in 3SR, NASBA, transcription-based or any other primer extension amplification reactions. For detection of amplification products, amplification primers comprising the target binding sequences disclosed herein may be labeled as is known in the art, or labeled detector primers comprising the disclosed target binding sequences may be used in conjunction with the amplification primers as described in U.S. Pat. No. 5,547,861; U.S. Pat. No. 5,928,869; U.S. Pat. No. 5,593,867; U.S. Pat. No. 5,550,025; U.S. Pat. No. 5,935,791; U.S. Pat. No. 5,888,739 and U.S. Pat. No. 5,846,726 for real-time homogeneous detection of amplification. Such detector primers may comprise a directly or indirectly detectable sequence which does not initially hybridize to the target but which facilitates detection of the detector primer once it has hybridized to the target and been extended. For example, such detectable sequences may be sequences which form a secondary structure, sequences which contain a restriction site, or linear sequences which are detected by hybridization of their complements to a labeled oligonucleotide (sometimes referred to as a reporter probe) as is known in the art. Alternatively, the amplification products may be detected post-amplification by hybridization of a probe selected from any of the target binding sequences.disclosed herein which fall between a selected set of amplification primers.

It is to be understood that an oligonucleotide according to the invention which consists of a target binding sequence and, optionally, either a sequence required for a selected amplification reaction or a sequence required for a selected detection reaction may also include certain other sequences which serve as spacers, linkers, sequences for labeling or binding of an enzyme, etc. Such additional sequences are typically known to be necessary to obtain optimum function of the oligonucleotide in the selected reaction and are intended to be included by the term "consisting of."

EXAMPLE

Use of the primers and probes of the invention may be exemplified using an SDA reaction to detect HBV. For such a reaction, one "left" amplification primer is selected from SEQ ID NOs:1–3 and one "right" amplification primer ("AR") is selected from SEQ ID NOs:4–6. A detector primer is also selected from SEQ ID NOs:7–15, and the hairpin is labeled with a donor/quencher dye pair as is known in the art for detection of target amplification. Fluorescein and dabcyl are preferred dyes for this purpose. Finally, SEQ ID NO:16 serves as the "left" bumper primer and either SEQ ID NO:17 or SEQ ID NO:18 may be selected as the "right" bumper primer. SDA is preferably performed at about 52° C. as described in U.S. Pat. No. 5,648,211 using the selected detector primer to provide detection of the target during amplification as described in U.S. Pat. No. Nos. 5,919,630; 5,928,869 and 5,958,700.

Donor fluorescence is monitored during the amplification reaction. In the presence of HBV target nucleic acids, donor fluorescence will increase as the hairpin holding the donor and quencher in close proximity is unfolded. In the absence of target, fluorescence will remain consistently low throughout the reaction. An increase in flourescence or a failure of fluorescence to change substantially indicate the presence or absence of HBV target, respectively. Typically, the generation of a relatively higher amount of flourescence indicates a higher initial level of target.

What is claimed is:

1. An oligonucleotide comprising a target binding sequence selected from the group consisting of the target binding sequences corresponding to HBV1AL1 (SEQ ID NO:1), and HBV1AR1 (SEQ ID NO:4), and optionally, a sequence required for an amplification reaction.

2. The oligonucleotide of claim 1 wherein the sequence required for the amplification reaction is a restriction endonuclease recognition site which is nickable by a restriction endonuclease.

3. The oligonucleotide of claim 2 selected from the group consisting of HBV1AL1 (SEQ ID NO:1) and HBV1AR1 (SEQ ID NO:4).

* * * * *

SEQUENCE LISTING

```
<160> NUMBER OF SEQ ID NOS: 20

<210> SEQ ID NO 1
<211> LENGTH: 39
<212> TYPE: DNA
<213> ORGANISM: Hepatitis B virus

<400> SEQUENCE: 1
cgattccgct ccagacttct cgggccctg ctcgtgtta                              39

<210> SEQ ID NO 2
<211> LENGTH: 38
<212> TYPE: DNA
<213> ORGANISM: Hepatitis B virus

<400> SEQUENCE: 2
cgattccgct ccagacttct cgggccctg ctcgtgtt                               38

<210> SEQ ID NO 3
<211> LENGTH: 39
<212> TYPE: DNA
<213> ORGANISM: Hepatitis B virus

<400> SEQUENCE: 3
cgattccgct ccagacttct cgggacccct gctcgtgtt                             39

<210> SEQ ID NO 4
<211> LENGTH: 39
<212> TYPE: DNA
<213> ORGANISM: Hepatitis B virus

<400> SEQUENCE: 4
accgcatcga atgcatgtct cgggggtatt gtgaggatt                             39

<210> SEQ ID NO 5
```

-continued

```
<211> LENGTH: 41
<212> TYPE: DNA
<213> ORGANISM: Hepatitis B virus

<400> SEQUENCE: 5
accgcatcga atgcatgtct cgggtgagga ttattgtcaa c                    41

<210> SEQ ID NO 6
<211> LENGTH: 37
<212> TYPE: DNA
<213> ORGANISM: Hepatitis B virus

<400> SEQUENCE: 6
accgcatcga atgcatgtct cgggtattgt gaggatt                         37

<210> SEQ ID NO 7
<211> LENGTH: 38
<212> TYPE: DNA
<213> ORGANISM: Hepatitis B virus

<400> SEQUENCE: 7
tagcacccga gtgctaggcg gggttttttct tgttgaca                       38

<210> SEQ ID NO 8
<211> LENGTH: 39
<212> TYPE: DNA
<213> ORGANISM: Hepatitis B virus

<400> SEQUENCE: 8
tagcacccga gtgctaggcg gggttttttct tgttgacaa                      39

<210> SEQ ID NO 9
<211> LENGTH: 39
<212> TYPE: DNA
<213> ORGANISM: Hepatitis B virus

<400> SEQUENCE: 9
tagcacccga gtgctttgtc aacaagaaaa accccgcct                       39

<210> SEQ ID NO 10
<211> LENGTH: 32
<212> TYPE: DNA
<213> ORGANISM: Hepatitis B virus

<400> SEQUENCE: 10
tagcacccga gtgctgctcg tgttacaggc gg                              32

<210> SEQ ID NO 11
<211> LENGTH: 31
<212> TYPE: DNA
<213> ORGANISM: Hepatitis B virus

<400> SEQUENCE: 11
tagcacccga gtgctctcgt gttacaggcg g                               31

<210> SEQ ID NO 12
<211> LENGTH: 35
<212> TYPE: DNA
<213> ORGANISM: Hepatitis B virus

<400> SEQUENCE: 12
tagcacccga gtgctttgtg aggattcttg tcaac                           35
```

```
<210> SEQ ID NO 13
<211> LENGTH: 35
<212> TYPE: DNA
<213> ORGANISM: Hepatitis B virus

<400> SEQUENCE: 13
tagcacccga gtgctttgtg aggattattg tcaac                        35

<210> SEQ ID NO 14
<211> LENGTH: 33
<212> TYPE: DNA
<213> ORGANISM: Hepatitis B virus

<400> SEQUENCE: 14
tagcacccga gtgctgtgag gattcttgtc aac                          33

<210> SEQ ID NO 15
<211> LENGTH: 33
<212> TYPE: DNA
<213> ORGANISM: Hepatitis B virus

<400> SEQUENCE: 15
tagcacccga gtgctgtgag gattattgtc aac                          33

<210> SEQ ID NO 16
<211> LENGTH: 15
<212> TYPE: DNA
<213> ORGANISM: Hepatitis B virus

<400> SEQUENCE: 16
catcaggatt cctag                                              15

<210> SEQ ID NO 17
<211> LENGTH: 14
<212> TYPE: DNA
<213> ORGANISM: Hepatitis B virus

<400> SEQUENCE: 17
acgagtctag actc                                               14

<210> SEQ ID NO 18
<211> LENGTH: 16
<212> TYPE: DNA
<213> ORGANISM: Hepatitis B virus

<400> SEQUENCE: 18
aaaattgaga gaagtc                                             16

<210> SEQ ID NO 19
<211> LENGTH: 17
<212> TYPE: DNA
<213> ORGANISM: Hepatitis B virus

<400> SEQUENCE: 19 ggttttctt gttgaca                                             17

<210> SEQ ID NO 20
<211> LENGTH: 16
<212> TYPE: DNA
<213> ORGANISM: Hepatitis B virus

<400> SEQUENCE: 20
aagaaaaacc ccgcct                                             16
```